United States Patent [19]
Bendel et al.

[11] Patent Number: 5,242,458
[45] Date of Patent: Sep. 7, 1993

[54] SUTURE NEEDLE HOLDER FOR ENDOSCOPIC USE

[75] Inventors: Lee P. Bendel, Lebanon; Surjit S. Gill, Bridgewater; William McJames, Belle Meade, all of N.J.; Barry McKernan, Marietta, Ga.

[73] Assignee: Ethicon, Inc., Somerville, N.J.

[21] Appl. No.: 776,153

[22] Filed: Oct. 15, 1991

[51] Int. Cl.$^5$ .............................................. A61B 17/00
[52] U.S. Cl. ............................................ 606/147; 606/205
[58] Field of Search ............... 606/147, 148, 142, 139, 606/143, 205

[56] References Cited

U.S. PATENT DOCUMENTS

| | | | |
|---|---|---|---|
| H1028 | 3/1992 | Falk et al. | 606/205 |
| 2,363,334 | 11/1944 | Jones | 606/147 |
| 2,790,437 | 4/1957 | Moore | 128/751 |
| 3,503,396 | 3/1970 | Pierie et al. | 606/207 |
| 3,913,586 | 10/1975 | Baumgarten | 606/205 |
| 4,120,302 | 10/1978 | Ziegler | 606/207 |
| 4,271,838 | 6/1981 | Lasner et al. | 606/147 |
| 4,491,135 | 1/1985 | Klein | 606/147 |
| 4,643,190 | 2/1987 | Heimberger | 606/205 |
| 4,898,157 | 2/1990 | Messroghli et al. | 606/147 |
| 4,950,273 | 8/1990 | Briggs | 606/205 |

Primary Examiner—Stephen C. Pellegrino
Assistant Examiner—Gary Jackson
Attorney, Agent, or Firm—Paul A. Coletti

[57] ABSTRACT

A suture needle holder is described with a ratcheting mechanism and a optimized set of jaws. These jaws have nitinol inserts for deformability around a suture needle. The shaft of the endoscopic suture needle holder is rotatable to allow placement of the jaws. Also, operation may take place along only one axis, by making the handles parallel to the shaft axis and the jaws which grip the suture needle.

9 Claims, 3 Drawing Sheets

SUTURE NEEDLE HOLDER FOR ENDOSCOPIC USE

FIELD OF THE INVENTION

Generally, this invention relates to suture needle holders. More specifically, this invention relates to endoscopic suture needle holders. Most specifically, this invention relates to suture needle holders designed for endoscopic use wherein the needle is easily maintained within the holder, and the holder is easily manipulable within an endoscopic trocar cannula.

BACKGROUND OF THE INVENTION

Currently, there are very few suture needle holders which are applicable for endoscopic purposes. And, in fact, any current endoscopic needle holders have quite a few deficiencies. For instance, most endoscopic needle holders are able to hold straight suture needles, but curved suture needles present a difficulty. This is generally because the curved needles, when placed within current needle holder jaws, tend to rotate within the pair of jaws which hold the needle.

In addition, current needle holders do not have the capability of placing a strong and stable grip on the needle. Therefore, in use, these needle holders tend to damage suture material, because the needle may tend to slip within the needle holder jaws, so that the suture comes into to contact with the needle holders. This is generally due to the lack of pressure and/or lack of control of the pressure exerted upon the needle.

In addition, some needle holders are not capable of holding needles within tight endoscopic spaces. This is generally due to the design of the needle holder jaws. Currently, needle holder jaws are deficient in that they are relatively incapable of maintaining the needle, and yet fit within tight spaces. Finally, there is a perceived deficiency in that current needle holders are neither rotatable, nor fixedly rotatable within a trocar cannula. That is, without rotatability, these endoscopic suture needle holders are less easy to manipulate than may be desired. These needle holders are used in such narrow confines, that it is desirable to be able to reliably rotate the suture needle within this confine. Of course, it is also necessary to lock the mechanism after rotation, so the needle holder must be capable of maintaining a rigid position when locked.

SUMMARY OF THE INVENTION

Accordingly, it is the object of the invention to provide a reliably adjustable suture needle holder. This needle holder should be capable of reliably applying pressure to the suture needle to be held, and also reliably manipulating the suture needle when emplaced within a trocar cannula and in pneumoperitoneum.

It is another object to the invention to provide a suture needle holder with an adjustable clamping force.

It is yet another object of the invention to provide a needle holder which is able to rotatably fit within the abdomen through a cannula.

It is yet another object of the invention to provide a suture needle holder which will not damage the suture while inserting the needle into a trocar cannula with the suture attached.

Yet another object of the invention is to provide for a suture needle holder which is rotatable and locking either before or during insertion within a trocar cannula.

Finally, it is an object of the invention to provide for a suture needle holder having jaws which have a low modulus of elasticity combined with high yield strength in order to prevent slippage of the suture needle after insertion.

These and other objects of the invention are accomplished in an endoscopic needle holder with an actuating mechanism remotely connected to a pair needle holding jaws. Each of the jaws have a serrated surface for gripping the needle and each of the jaws have a needle clamping profile which comprises a pair of walls such that the walls approach each other toward the distal end of the jaws. The actuating mechanism is remotely connected to the pair of jaws, and the actuating mechanism may formed into a handle-shaped mechanism which may be locked or rotated while holding the jaws within the needle. Also, the shaft of the needle holder is rotatable about its longitudinal axis, so that the jaws themselves may rotate in orientation. At the desired moment, the shaft may be locked so that the jaws stay firmly in place during emplacement of a suture. Finally, the jaws themselves are created from a serrated insert, generally formed from nitinol, which allows secure grip on the needle, and yet no damage to the needle.

The objects of the present invention will be more readily understood from the attached Detailed Description of the Drawings taken in combination with the Detailed Description of the Invention.

DETAILED DESCRIPTION OF THE DRAWINGS

DETAILED DESCRIPTION OF THE INVENTION

Figure 1:
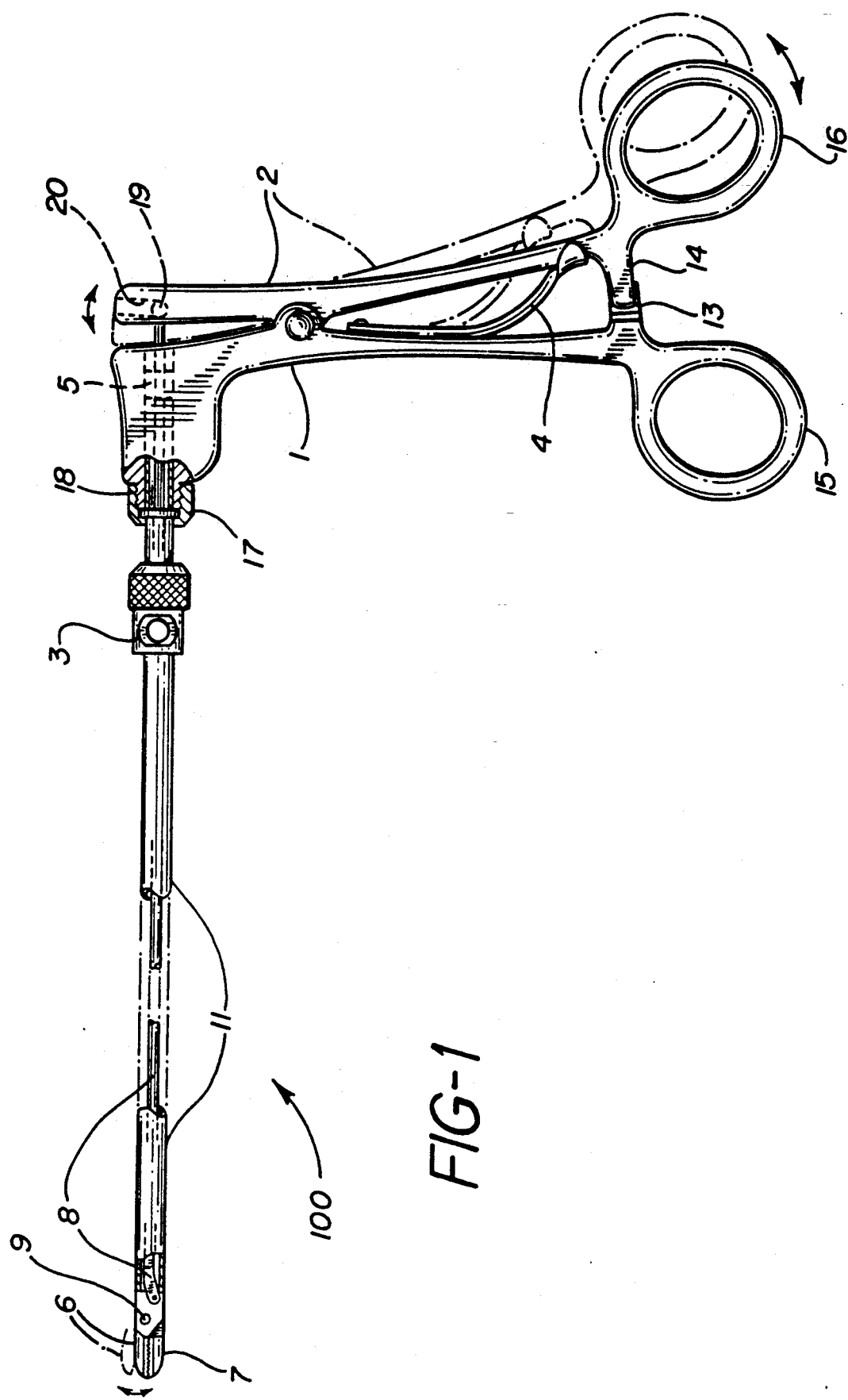
FIG. 1 is a side elevation view of an endoscopic needle holder of the present invention.

As seen in FIG. 1, there is described an endoscopic needle holder 100 which contains a pair of serrated jaws 6, 7 for applying a firm grip. One of the jaws 7 is stationary, while the other jaw 6 is pivotable at pivot 9, with relation to the first jaw 7. This pivotable jaw 6 is controlled by a cable 8 extending the entire length of the shaft 11 of the endoscopic needle holder 100. It is this shaft 11 which is emplaced within the cannula of a surgical trocar, for instance the Endopath ™ trocar currently marketed by Ethicon, Inc., Somerville, NJ.

The rotatable and pivotable jaws of the endoscopic needle holder 100 are held within a handle mechanism. This handle mechanism contains a support handle, which maintains the shaft 11 on a longitudinal axis. Also, this holder mechanism contains an actuating handle 2 which is connected with the cable 8, so that it actuates the pivotable jaw 6 of the suture needle holder 100. These handles 1, 2 are attachable by a ratcheting system 13, 14 as seen at the base of the handle so that when the jaws are closed, the handles 1, 2 may be locked together.

The ratcheting system 13, 14 ensures easy locking or unlocking of the handles 1, 2 and provides an adjustable force for holding the needle in the jaw. This force adjustment is necessary to hold various sizes and shapes of needles for different body tissue and for smooth penetration of soft as well as hard tissue. Once the ratchet teeth 13 are engaged on lock 14, the surgeon knows that the locked handles 1, 2 are conveniently holding the suture needle and may easily and readily manipulate the needle to pass through the tissue. The ratchet teeth 13 may be readily unlocked with one hand by positioning a finger inside the ring 15 of one handle 1 and another finger within the ring 16 of the opposite handle 2 and pushing the ratchet 13, 14 apart while exerting a scissor-like force on the ratchets.

Each of the handles 1, 2 include finger rings 15, 16 which are useful for positioning and operating the jaws. Also, a small leaf spring 4 is positioned between the handles 1, 2 to insure that jaws 6, 7 are normally in their open position, and that there is no interference with a surgeon's manipulation of the instrument with the jaws 6, 7 closed.

Finally, the handle portion 1, 2 can easily be disassembled from the shaft portion by unscrewing the collar 17 on the shaft 8 connected to threaded opening 18 of handle 1. Then, ball 19 may be lifted from socket 20 in handle 2. Bumper or absorber 5 is made of rubber and is connected to shaft 8 to cause smooth interplay of the handles 1,2 with shaft 8 contained therein. This combination ensures interchangeability of shafts of the different sized needle holders.

As further seen in FIG. 1, the shaft 8 is placed in a cannula along its longitudinal axis, which is generally 5 mm in diameter, allowing the shaft to conveniently be inserted within a trocar cannula. This shaft 8 contains a luer locking mechanism 3 for attachment to an insufflation device, to provide insufflation force to the cannula.

It is important to notice that the shaft is rotatable in relation to the handles. This feature allows the surgeon to manipulate the needle holder within the abdominal cavity without moving the handle portions 1, 2. The shaft is locked in its normal operating position by the collar 17 on the shaft threaded into screw 18 on handle 1, so that operation is readily possible. Also, the luer portion 3 of the shaft 8 allows for easy cleaning after usage.

Importantly, the jaws 6, 7 of the invention are serrated so that a firm grip is placed on a curved needle and so that a curved needle may obtain a smooth passage through tissue without turning or slipping of the needle through the jaws 6, 7. The density of the jaw serrations prevents suture damage while passing the needle through the trocar cannula. The jaws 6, 7 are created so that they are narrow at their forward-most end so that a needle may be held close to the point in which the needle is passed through thick tissue. The width of the jaws is gradually enlarged to provide a proper base for placing the jaw and needle held therein within tissue. The jaws 6, 7 are created with metallic inserts I on which the serrations are formed. These inserts I are generally formed from nitinol, which has a low modulus of elasticity and a high yield strength. This combination allows the inserts to deform around the needle during holding of the needle so that slippage is prevented. After the needle is released from the holder, the insert I resumes its original shape, and damage to the needle does not occur.

Figure 2:
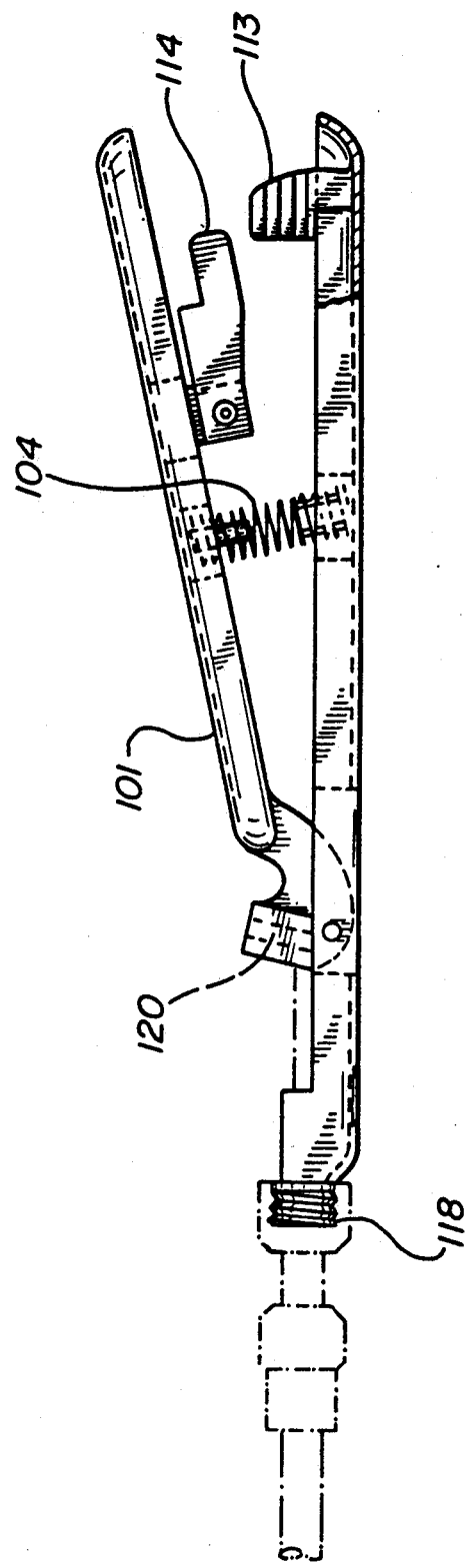
FIG. 2 is a side view of an alternate handle for endoscopic needle holder of the invention.
Figure 3:
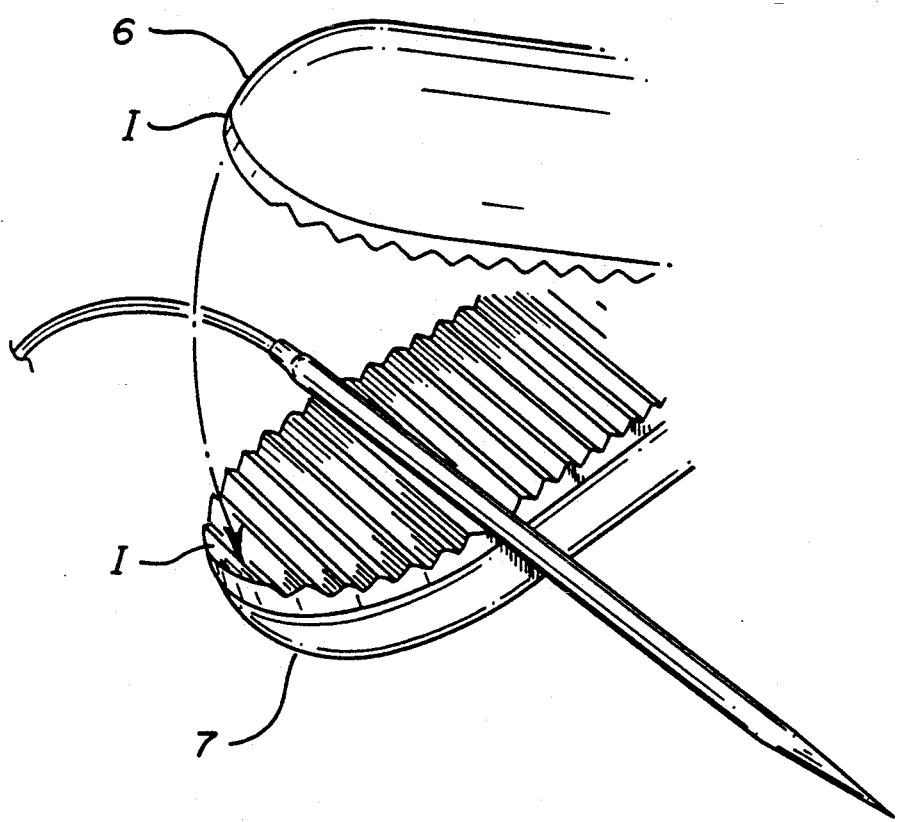
FIG. 3 is an enlarged perspective view of the jaws containing nitinol inserts.

As seen in FIG. 2, there is also the possibility that handles 101, 102 may be connected to shaft 8 so that the handles be along an axis generally parallel to the axis of shaft 8. Connection is made to shaft 8 at threaded opening 118 and socket 120. A spring 104 permits handles 101, 102 to remain in an opened position. Ratchets 113, 114 lock in the same manner as ratchets 13, 14. In this manner, however, the use of the needle holder is entirely along the same axis.

In operation, therefore, the needle holder 100 of this invention is created so that it may have its jaws 6, 7 placed about a suture needle. Then the handles 1, 2 are pulled together so that the suture needle holder jaws grip the suture needle. If desired, the ratcheting mechanism 13, 14 may be used so that the amount of force on the needle varies. Also, because the inserts in the jaws 6, 7 are made from nitinol, the jaws deform somewhat around the needle as the needle is placed within the jaws. If desired, the needle may be rotated by rotating the longitudinal shaft 8 of the suture needle holder about handles 1, 2. When the needle is in its proper desired needle position, the shaft 8 should be locked at collar 17 and for positioning through a trocar cannula. Now, with the needle ready to use, and the needle holder placed down the cannula, suturing begins. After the needle is properly placed within tissue, the needle holder can be released and made to regrip the tissue so that it can be either passed again through tissue or removed through the trocar cannula.

The objects of the invention are to be understood from the attached claims and their equivalents.

What is claimed is:

1. An endoscopic suture needle holder comprising an actuating mechanism remotely connected to a pair of needle holding jaws wherein said actuating mechanism may be locked with said jaws holding said needle and said jaws characterized in that each of said jaws containing a base and a needle facing insert, a said insert attached to a said base, and each of said inserts on said jaws placed in opposed relationship toward one another so as to grip a suture needle therebetween, each said insert formed from nitinol such that the nitinol deforms around the needle when said needle is placed between said inserts and when said jaws are in a closed position.

2. The needle holder of claim 1 wherein said locking takes place on a ratchet system connected to said actuating mechanism.

3. The needle holder of claim 2 wherein said ratchet system exerts a discriminate set of forces on said needle through said jaws.

4. The needle holder of claim 1 wherein said actuating mechanism is a pair of handles, one of said handles pivotable about the other, and one said handle connected by a cable to a first of said jaws, such that when said handle pivots, said cable causes said first jaw to pivot about the second of said jaws.

5. The needle holder of claim 1, further having an actuating mechanism connected to a pair of needle holding jaws, by a shaft, said shaft fixedly holding one of said jaws, and said shaft rotatable about its longitudinal axis.

6. An endoscopic needle holding mechanism having an actuating mechanism connected to a pair of needle holding jaws, by a shaft, said shaft fixedly holding one of said jaws, and said shaft rotatable about its longitudinal axis and said jaws characterized in that each of said jaws contain a base and a needle facing insert, a said insert attached to a said base, and each of said inserts on said jaws placed in opposed relationship toward one another so as to grip a needle therebetween, each said insert formed from nitinol such that the nitinol deforms around the needle when said needle is placed between said inserts and when said jaws are in a closed position.

7. The needle holder of claim 6 wherein said shaft contains a clamping mechanism to clamp said shaft into place after rotation about said axis.

8. The needle holder of claim 6 further comprising an actuating mechanism remotely connected to a pair of needling holding jaws wherein said actuating mechanism may be locked with said jaws holding said needle.

9. The needle holder of claim 8 wherein said actuating mechanism is a pair of handles, one of said handles pivotable about the other, and one said handle connected by a cable to a first of said jaws, such that when said handle pivots, said cable causes said first jaw to pivot about the second of said jaws.

* * * * *